United States Patent [19]

Guillemette et al.

[11] 4,282,161

[45] Aug. 4, 1981

[54] NOVEL PURIFICATION PROCESS

[76] Inventors: Armand Guillemette, 17, Avenue d'Alsace-Lorraine, 93130 Noisy-le-Sec; Abel Francois, 139, Avenue Carnot, 93140 Bondy, both of France

[21] Appl. No.: 146,496

[22] Filed: May 5, 1980

[30] Foreign Application Priority Data

May 23, 1979 [FR] France .............................. 79 13117

[51] Int. Cl.³ .............................................. C07J 9/00
[52] U.S. Cl. .................................................. 260/397.1
[58] Field of Search ...................................... 260/397.1

[56] References Cited

PUBLICATIONS

Japan Medical News, Mar. (1963) Overseas Free Edition, pp. 10-11.
Chem. Abstracts, vol. 87, (1977) Par. 168,277r.

*Primary Examiner*—Elbert L. Roberts
*Attorney, Agent, or Firm*—Hammond & Littell, Weissenberger and Muserlian

[57] ABSTRACT

A novel process for the purification of ursodesoxycholic acid comprising reacting an aqueous solution of an alkali metal salt of ursodesoxycholic acid in the presence of chloroform with an acid and recovering crystalline ursodesoxycholic acid.

6 Claims, No Drawings

NOVEL PURIFICATION PROCESS

STATE OF THE ART

Ursodesoxycholic acid or 3α,7α-dihydroxy-5β-cholanic acid is used for dissolution of bile calculus or gallstones and is used for the treatment of bile lithiasis. In a classic manner, ursodesoxycholanic acid is prepared from chenodesoxycholic acid [Chem. Ab, Vol. 51 (1957), p. 17965] which is prepared from cholic acid [J.A.C.S., Vol. 72 (1950), p. 5530] which in turn is extracted from animal bile. In these preparations, raw ursodesoxycholanic acid contains a certain number of impurities such as other bile acids, especially chenodesoxycholic acid and derivatives of bile acids formed in the synthesis. The presence of these impurities in a product destined for prolonged administration as in the case of ursodesoxycholanic acid raises the problem of undesirable side effects.

It is important to have a purification process for ursodesoxycholanic acid which permits one to obtain the product in a very high degree of purity. Japanese patent application Ser. No. 154,864/1975 describes the purification of ursodesoxycholanic acid by forming the methyl ester thereof, crystallizing the said ester from an organic solvent and hydrolyzing the latter to the free acid.

OBJECTS OF THE INVENTION

It is an object of the invention to provide an improved process for the purification of ursodesoxycholanic acid on an industrial scale with improved yields.

It is a further object of the invention to provide a purified ursodesoxycholanic acid.

These and other objects and advantages of the invention will become obvious from the following detailed description.

THE INVENTION

The novel process of the invention for the purification of ursodesoxycholanic acid comprises reacting an aqueous solution of an alkali metal salt of ursodesoxycholic acid in the presence of chloroform with an acid and recovering crystalline ursodesoxycholic acid.

Examples of suitable alkali metal salts of ursodesoxycholanic acid are the sodium, potassium and lithium salts, preferably the sodium salt but equally useful is the lithium salt. Examples of suitable acids for treating the alkali metal salts are mineral acids such as hydrochloric acid, sulfuric acid and phosphoric acid, with hydrochloric acid being preferred. The crystalline acid which crystallizes in the process is preferably dried such as by heating under reduced pressure or with ventilation.

The starting alkali metal ursodesoxycholate may be prepared by esterifying raw ursodesoxycholic acid with methanol followed by crystallization of the methyl ester and saponification of the ester. In a preferred embodiment, the methyl ester is crystallized from ethyl acetate. Ethyl acetate is preferred as the crystallization solvent to other solvents such as methanol used by Japanese patent application Ser. No. 154,864/1975 cited above as it permits a greater purification of the ester with a higher degree of crystallization.

The alkali metal salt of ursodesoxycholic acid may also be prepared beginning from chenodesoxycholic acid by the process of Chem. Abs., Vol. 51 (1957), p. 17965 by effecting the reduction of 3α-hydroxy-7-keto-cholanic acid in the last step with an alkali metal. The said alkali metal may be sodium used in the presence of tert-butanol as in Japanese patent application Ser. No. 154,865/1975. However, the reduction of 3α-hydroxy-7-keto-cholanic acid may also be effected with lithium in liquid ammonia in the presence of an alkanol such as methanol with the reaction preferably being effected in an organic solvent such as tetrahydrofuran.

Another facet of the invention is purified ursodesoxycholic acid containing less than 0.50% of chenodesoxycholic and especially less than 0.25% by weight of chenodesoxycholic acid. The said ursodesoxycholic acid is in the form of a product crystallized from chloroform.

In the following examples there are described several preferred examples to illustrate the invention. However, it should be understood that the invention is not intended to be limited to the specific embodiments.

EXAMPLE 1

A solution of 1.320 kg of raw ursodesoxycholic acid containing about 8% of chenodesoxycholic acid in 5.280 liters of methanol was stirred at 20° C. for about 15 minutes and then 132 ml of 66° Be sulfuric acid were added thereto over 15 minutes with stirring. The mixture was stirred for 2 hours and then a mixture of 3.960 liters of demineralized water, 0.400 kg of sodium bicarbonate, 1.320 kg of ice and 3.960 liters of methylene chloride were added thereto. The mixture was stirred for 15 minutes and the decanted aqueous phase was extracted with methylene chloride. The methylene chloride solution was washed with water and the wash waters were extracted with methylene chloride. The combined organic phases were dried over anhydrous sodium sulfate, treated with activated carbon and were vacuum filtered. The filter was rinsed with methylene chloride and the filtrate was evaporated to dryness. The residue was taken up in 2.640 liters of ethyl acetate and the mixture was distilled at ordinary pressure to a volume of 1.320 liters and was then evaporated to dryness under reduced pressure. The residue was taken up in 7.920 liters of ethyl acetate and the mixture was refluxed with stirring until total dissolution occured and was then distilled at ordinary pressure to a volume of 1.320 liters. The mixture was cooled to 60° C. and held there for 18 hours and was then cooled to 0° to 5° C. The mixture was held at 0° to 5° C. for one hour and the precipitate was empasted 3 times with 0.660 liters of ethyl acetate at 0° to 5° C. and dried at 60° C. to obtain 1.134 kg of methyl ursodesoxycholate melting at 158° C. From the crystallization liquor and wash water, another 62 g of methyl ursodesoxycholate were obtained for a total yield of 1.196 kg.

The said 1.196 kg of the methyl ester were dissolved with stirring at 20° to 25° C. in 5.980 liters of methanol and a solution of 0.360 liters of 36° Be sodium hydroxide solution in 7.180 liters of demineralized water was added thereto. The mixture was refluxed with good stirring for one hour and was then cooled to 50° to 60° C. and was vacuum filtered. The filter was washed with 1.196 liters of methanol at 50° to 60° C. and the filtrate was distilled at ordinary pressure. The aqueous concentrate was added to 3.590 liters of water and after cooling the mixture to 27°±2° C., 5.980 liters of chloroform were added thereto. Then, 1,500 liters of a solution of 14% by volume of 22° Be hydrochloric acid and 86% by volume of demineralized water were added over 30 minutes with stirring at 27°±2° C. to the mixture and the mixture was stirred at 27°±2° C. for 30 minutes. Then, 1.345 liters of the same hydrochloric acid solution were added thereto over 30 minutes and the mixture was stirred at 27°±2° C. for 2 hours and was vacuum filtered. The crystalline product was empasted with chloroform at 27°±2° C. and then with demineralized water and was dried at 60° C. to obtain 1.130 kg of ursodesoxycholic acid. Another 25 g of the product were recovered from the crystallization liquors and it had a specific rotation of $[\alpha]_D^{20} = +30.5 \pm 0.5°$ (c=5% in ethanol). Thin layer chromatography showed that the product contained 0.25% of chenodesoxycholic acid and about 0.25% of bile acids or other derivatives of ursodesoxycholic acid and chenodesoxycholic acid.

EXAMPLE 2

A mixture of 9.180 liters of tetrahydrofuran and 0.460 liters of methanol at −10° C. and 7.650 liters of liquid ammonia was stirred for one hour at −35° to −40° C. and then 1.530 kg of 3α-hydroxy-7-keto-cholanic acid were added thereto over 15 minutes. 111 g of lithium were added with stirring at −35° to −38° C. over one hour to the mixture which was then stirred for one hour at −35° to −38° C. 1.530 liters of methanol were added to the mixture over 15 minutes and then 1.530 liters of demineralized water were added to the mixture over 15 minutes and stirring at 20° C. The ammonia was distilled and when the majority of the ammonia was evaporated, 7.650 liters of water were added to the mixture with stirring at 27°±2° C. Then, the tetrahydrofuran-methanol mixture was distilled off under reduced pressure at a bath temperature of 60° C. while progressively adding 1.530 liters of demineralized water to keep the volume constant and after cooling the mixture to about 27° C., 15,300 liters of water were added thereto. 7.650 liters of chloroform were added to the mixture with stirring and then 3,060 liters of 22° Be hydrochloric acid were added thereto over one hour at 27°±2° C. until a pH of 7 was obtained. At this point, acid addition was halted and the mixture was stirred for 30 minutes at 27°±2° C. after which the rest of the acid was added. The mixture was stirred for 2 hours at 27°±2° C. and was vacuum filtered with cotton cloth. The damp product was suspended in 2.300 liters of chloroform at 27°±2° C. and the suspension was stirred at 27°±2° C. for 15 minutes and was vacuum filtered. The product was resuspended in 2300 liters of chloroform at 27°±2° C. for 15 minutes and the suspension was vacuum filtered. The product was washed several times with water and dried at 60° C. to obtain 1.320 g of ursodesoxycholic acid melting at 198° C. and having a specific rotation of $[\alpha]_D^{20} = +55.5° \pm 0.5°$ (c=5% in ethanol).

Various modifications of the products and processes of the invention may be made without departing from the spirit or scope thereof and it is to be understood that the invention is intended to be limited only as defined in the appended claims.

We claim

1. A process for the purification of ursodesoxycholic acid comprising reacting an aqueous solution of an alkali metal salt of ursodesoxycholic acid in the presence of chloroform with an acid and recovering crystalline ursodesoxycholic acid.

2. The process of claim 1 wherein the alkali metal salt is sodium salt.

3. The process of claim 1 wherein the alkali metal salt is the lithium salt.

4. The process of claim 1 wherein the acid is hydrochloric acid.

5. The process of claim 1 wherein the crystalline ursodesoxycholic acid is dried.

6. The process of claim 1 wherein the alkali metal salt of ursodesoxycholic acid is obtained by esterification of raw ursodesoxycholic acid with methanol, crystallizing the resulting methyl ester from ethyl acetate and saponifying the ester with an alkali metal base.

* * * * *

UNITED STATES PATENT AND TRADEMARK OFFICE
CERTIFICATE OF CORRECTION

PATENT NO. : 4,282,161

DATED : August 4, 1981

INVENTOR(S) : ARMAND GUILLEMETTE and ABEL FRANCOIS

It is certified that error appears in the above—identified patent and that said Letters Patent is hereby corrected as shown below:

Column 2, line 2: "tert -butanol" should read -- tert.-butanol --.

Column 4, line 11: "ursodesox-" should read -- ursodesoxy- --.

line 12: "ycholic" should read -- cholic --.

Signed and Sealed this

Twenty-sixth Day of January 1982

[SEAL]

Attest:

GERALD J. MOSSINGHOFF

*Attesting Officer*  *Commissioner of Patents and Trademarks*